(12) United States Patent
Podhajsky

(10) Patent No.: US 8,100,896 B2
(45) Date of Patent: Jan. 24, 2012

(54) METHOD FOR TREATMENT OF AN INTERVERTEBRAL DISC

(75) Inventor: Ronald J. Podhajsky, Boulder, CO (US)

(73) Assignee: Covidien AG (CH)

( * ) Notice: Subject to any disclaimer, the term of this patent is extended or adjusted under 35 U.S.C. 154(b) by 742 days.

(21) Appl. No.: 12/252,560

(22) Filed: Oct. 16, 2008

(65) Prior Publication Data

US 2009/0088671 A1    Apr. 2, 2009

Related U.S. Application Data

(63) Continuation of application No. 10/945,656, filed on Sep. 21, 2004, now abandoned.

(51) Int. Cl.
*A61B 18/04* (2006.01)
(52) U.S. Cl. ............. 606/33; 606/37; 607/101; 607/102
(58) Field of Classification Search .................... 606/33, 606/37, 41; 607/101–102
See application file for complete search history.

(56) References Cited

U.S. PATENT DOCUMENTS

| | | | |
|---|---|---|---|
| 4,411,266 A | 10/1983 | Cosman | |
| 5,095,915 A | 3/1992 | Engelson | |
| 5,190,050 A | 3/1993 | Nitzsche | |
| 5,315,996 A | 5/1994 | Lundquist | |
| 5,334,145 A | 8/1994 | Lundquist et al. | |
| 5,404,886 A | 4/1995 | Vance | |
| 5,433,739 A | 7/1995 | Sluijter et al. | |
| 5,437,288 A | 8/1995 | Schwartz et al. | |
| 5,477,856 A | 12/1995 | Lundquist | |
| 5,497,785 A | 3/1996 | Viera | |
| 5,571,147 A | 11/1996 | Sluijter et al. | |
| 5,573,520 A | 11/1996 | Schwartz et al. | |
| 5,823,994 A | 10/1998 | Sharkey et al. | |
| 5,876,356 A | 3/1999 | Viera et al. | |
| 5,908,395 A | 6/1999 | Stalker et al. | |
| 5,954,716 A | 9/1999 | Sharkey et al. | |
| 5,980,504 A | 11/1999 | Sharkey et al. | |
| 6,001,068 A | 12/1999 | Uchino et al. | |
| 6,004,279 A | 12/1999 | Crowley et al. | |
| 6,004,320 A | 12/1999 | Casscells et al. | |
| 6,007,533 A | 12/1999 | Casscells et al. | |
| 6,007,570 A | 12/1999 | Sharkey et al. | |
| 6,068,628 A | 5/2000 | Fanton et al. | |
| 6,073,051 A | 6/2000 | Sharkey et al. | |
| 6,095,149 A | 8/2000 | Sharkey et al. | |
| 6,126,682 A | 10/2000 | Sharkey et al. | |
| 6,179,836 B1 | 1/2001 | Eggers et al. | |
| 6,264,650 B1 | 7/2001 | Hovda et al. | |
| 6,264,651 B1 | 7/2001 | Underwood et al. | |
| 6,277,112 B1 | 8/2001 | Underwood et al. | |
| 6,283,961 B1 | 9/2001 | Underwood et al. | |
| 6,402,750 B1 | 6/2002 | Atkinson et al. | |
| 6,464,695 B2 | 10/2002 | Hovda et al. | |
| 6,468,270 B1 | 10/2002 | Hovda et al. | |
| 6,468,274 B1 | 10/2002 | Alleyne et al. | |

(Continued)

*Primary Examiner* — Roy Gibson

(57) ABSTRACT

The present disclosure is directed to methods for relieving pain associated with an intervertebral disc having a disc nucleus pulposus and an outer annulus fibrosus surrounding the nucleus pulposus. The method includes the steps of providing an elongated thermal or electromagnetic probe member having a flexible guidable region adjacent the distal end thereof; introducing the flexible guidable region of the probe into the annulus fibrosus of the intervertebral disc; and supplying thermal or electromagnetic energy, from an energy source, to heat or induce an electromagnetic field adjacent to the annulus fibrosus sufficient to produce a thermal or electromagnetic effect on the intervertebral disc. The flexible guidable region of the probe may be introduced at a location which is in relative close proximity to the region of intervertebral disc to be thermally or electromagnetically treated.

10 Claims, 6 Drawing Sheets

U.S. PATENT DOCUMENTS

| | | |
|---|---|---|
| 6,503,269 B2 | 1/2003 | Nield et al. |
| 6,540,741 B1 | 4/2003 | Underwood et al. |
| 6,547,810 B1 | 4/2003 | Sharkey et al. |
| 6,562,033 B2 | 5/2003 | Shah et al. |
| 6,579,291 B1 | 6/2003 | Keith et al. |
| 6,592,625 B2 | 7/2003 | Cauthen et al. |
| 6,602,248 B1 | 8/2003 | Sharps et al. |
| 6,604,003 B2 | 8/2003 | Fredricks et al. |
| 6,620,155 B2 | 9/2003 | Underwood et al. |
| 6,638,276 B2 | 10/2003 | Sharkey et al. |
| 6,645,203 B2 | 11/2003 | Sharkey et al. |
| 6,648,907 B2 | 11/2003 | Larnard et al. |
| 6,652,566 B2 | 11/2003 | Larnard et al. |
| 6,660,026 B2 | 12/2003 | Larnard et al. |
| 6,673,023 B2 | 1/2004 | Pflueger |
| 6,673,063 B2 | 1/2004 | Brett |
| 6,689,125 B1 | 2/2004 | Keith et al. |
| 6,699,242 B2 | 3/2004 | Heggeness |
| 6,712,811 B2 | 3/2004 | Underwood et al. |
| 6,726,684 B1 | 4/2004 | Woloszko et al. |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,743,200 B2 | 6/2004 | Larnard et al. |
| 6,749,605 B2 | 6/2004 | Ashley et al. |
| 6,752,767 B2 | 6/2004 | Turovskiy et al. |
| 6,757,565 B2 | 6/2004 | Sharkey et al. |
| 6,767,347 B2 | 7/2004 | Sharkey et al. |
| 6,772,012 B2 | 8/2004 | Ricart et al. |
| 6,805,695 B2 | 10/2004 | Keith et al. |
| 6,827,712 B2 | 12/2004 | Tovey et al. |
| 6,827,716 B2 | 12/2004 | Ryan et al. |
| 6,832,997 B2 | 12/2004 | Uchida et al. |
| 6,835,205 B2 | 12/2004 | Atkinson et al. |
| 6,837,884 B2 | 1/2005 | Woloszko |

METHOD FOR TREATMENT OF AN INTERVERTEBRAL DISC

CROSS REFERENCE TO RELATED PATENT APPLICATION

The present application is a Continuation of U.S. patent application Ser. No. 10/945,656, filed on Sep. 21, 2004 now abandoned, the entire content of which is hereby incorporated by reference.

BACKGROUND

1. Technical Field

The present disclosure relates to methods for treating intervertebral disc problems using percutaneous techniques without the need for major surgical intervention, and more particularly, to methods for the insertion of a cannula into the intervertebral disc and the insertion of a thermal probe into the disc material to heat the intervertebral disc thereby relieving and treating abnormalities or pain related to the disc.

2. Background of Related Art

The use of thermal therapy in and around the spinal column is known. Also, the insertion of cannula into the intervertebral discs is commonly done for injection of contrast mediums to implement X-ray discograms. This technique is used to detect or diagnose abnormalities or damage to the intervertebral disc. The use of heating of an intervertebral disc to relieve pain is described in U.S. Pat. No. 5,433,739, issued Jul. 18, 1995, and in U.S. Pat. No. 5,571,147, issued Nov. 5, 1996, the entire contents of each of which being incorporated herein by reference. In these patents, electrodes are described for either radiofrequency or resistive thermal heating of all or a portion of the intervertebral disc. Straight, curved, and flexible-tipped electrodes are described for this purpose. The thermal treatment of an intervertebral disc for the relief of back pain is also described within the patents cited above.

The use of a resistively heated probe adapted to be inserted into the intervertebral disc is described in U.S. Pat. No. 6,073,051, issued Jun. 6, 2000, the entire content of which is incorporated herein by reference. As seen in FIG. 1, U.S. Pat. No. 6,073,051, an apparatus or probe for treating intervertebral discs, the apparatus including a flexible catheter 14 which is introduced into the nucleus pulposus "N" and manipulated about (i.e., a functional element 16 of catheter 14 is introduced from a lateral side of nucleus pulposus "N", opposite the area to be treated, and extended around to the opposite lateral side of nucleus pulposus "N", adjacent to the area to be treated) an inner wall of the annulus fibrosus along annulus fibrosus/nucleus pulposus interface 28. Accordingly, functional element or intradiscal section 16 of catheter 14 delivers a therapeutic effect to the area of nucleus pulposus "N" to be treated, i.e., fissures "F".

It is desirable to treat the posterior or posterior/lateral portion of the intervertebral disc for the indication of mechanical degeneration of the disc and discogenic back pain. Pain can be derived from degeneration or compression of the intervertebral disc in its posterior or posterior/lateral portions. There is some innervation of the intervertebral disc near the surface of the disc and also within its outer portion known as the annulus fibrosus. Fissures or cracks within the disc caused by age, mechanical trauma, or disc degeneration are believed to be associated with painful symptoms.

Thus, a configuration of insertion cannula, to approach and enter the intervertebral disc, and a thermal probe to be built into or associated with said cannula, to adequately reach the posterior/lateral and posterior portions of the intervertebral disc, is desirable. Additionally, a novel method of introducing and advancing a thermal probe, toward the tissue to be treated, is also desirable.

SUMMARY

The present disclosure is directed generally to methods for the treatment of intervertebral discs. In particular, according to one aspect of the present disclosure, a method for relieving pain associated with an intervertebral disc having a disc nucleus pulposus and an outer annulus fibrosus surrounding the nucleus pulposus, is provided.

The method includes the steps of providing an elongated thermal or electromagnetic probe member. The probe member has proximal and distal ends and defines a longitudinal axis. The probe member further includes a flexible guidable region adjacent the distal end thereof.

The method further includes the step of introducing the flexible guidable region of the probe into the annulus fibrosus of the intervertebral disc. Preferably, the flexible guidable region of the probe is introduced at a location which is in relative close proximity to the region of intervertebral disc to be thermally or electromagnetically treated. The flexible guidable region of the probe is capable of bending to follow a generally arcuate path through the annulus fibrosus without entering the nucleus pulposus. Desirably, the step of introducing includes positioning the flexible guidable region of the probe adjacent the region of the intervertebral disc to be treated.

The method further includes the step of supplying thermal or electromagnetic energy, from an energy source, to heat or induce an electromagnetic field adjacent to the annulus fibrosus sufficient to produce a thermal or electromagnetic effect on the intervertebral disc.

The method may further include the step of positioning a cannula adjacent the region of the intervertebral disc to be treated; and passing the flexible guidable region of the probe through a lumen of the cannula.

It is envisioned that the cannula may include an arcuate portion adjacent a distal end thereof. Accordingly, during the step of introducing the flexible guidable region of the probe, the arcuate cannula portion may guide the flexible guidable region of the probe adjacent to the region to be treated.

The method may further include the step of angulating the arcuate portion of the cannula to a desired orientation within the intervertebral disc.

The method may still further include the step of monitoring impedance of tissue to detect variations in tissue-type to thereby facilitate positioning of the flexible guidable region of the probe.

The method further includes the steps of increasing an amplitude of thermal or electromagnetic energy supplied to the probe until indications of effect on the intervertebral disc are obtained; and noting the amplitude at which the indications of effect of the intervertebral disc are obtained.

Desirably, when the indications of effect of the intervertebral disc are obtained for amplitudes below about 0.75 volts, thermal energy at about 60° C. is applied. When the indications of effect of the intervertebral disc are obtained for amplitudes between about 0.75 volts and 1.25 volts, thermal energy at about 65° C. is applied. When the indications of effect of the intervertebral disc are obtained for amplitudes above about 1.25 volts, thermal energy at about 70° C. is applied.

According to another aspect of the present disclosure, the method includes the steps of introducing a thermal or electromagnetic transmitting element of a thermal probe into the intervertebral disc, at a location in close proximity to the region of the intervertebral disc to be treated; and supplying thermal or electromagnetic energy from an energy source to the thermal or electromagnetic transmitting element to produce a thermal or electromagnetic effect on the intervertebral disc.

Desirably, the probe includes a flexible guidable region. Accordingly, the method further includes the step of advancing the probe whereby the flexible guidable region of the probe follows a generally arcuate path. The step of advancing the probe may include passing the flexible guidable region along an arcuate path defined by natural striata of the annulus fibrosus. The step of advancing the probe may include extending the flexible guidable region across the region of the intervertebral disc to be treated.

BRIEF DESCRIPTION OF THE DRAWINGS

The features of the apparatus and method of the present disclosure will become more readily apparent and may be better understood by referring to the following detailed description of illustrative embodiments of the present disclosure, taken in conjunction with the accompanying drawings, wherein.

DETAILED DESCRIPTION OF PREFERRED EMBODIMENTS

Figure 1:
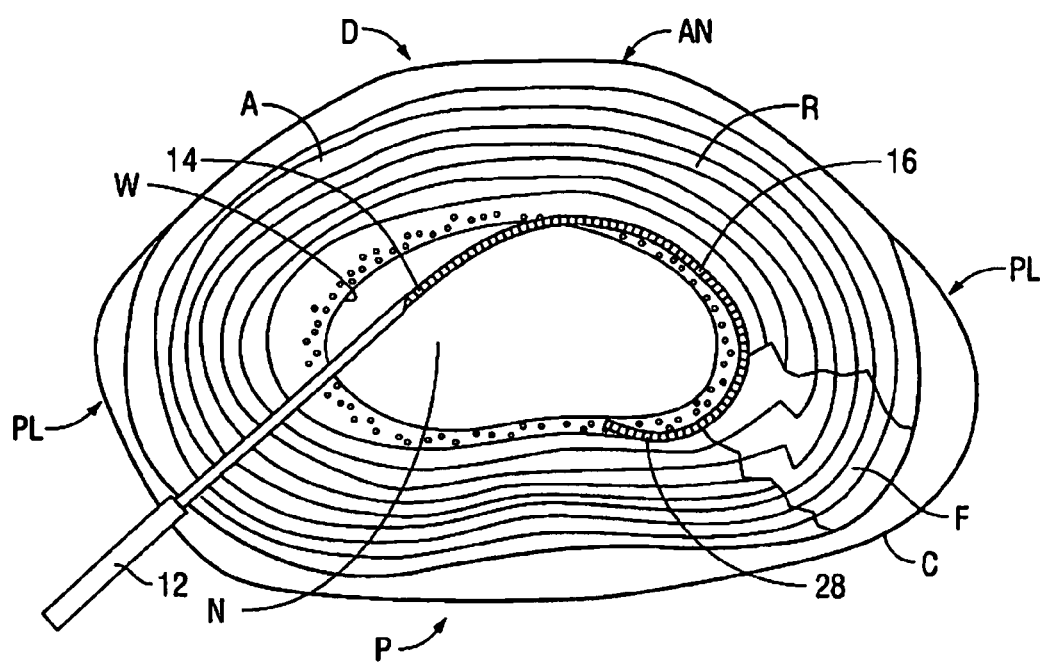
FIG. 1 is a cross-sectional view of an intervertebral disc with a portion of an intervertebral apparatus inserted therein according to a prior art method.

The present disclosure provides for an alternate and/or improved method of positioning an apparatus (e.g., a thermal probe) in an intervertebral disc targeted for treatment of intervertebral disc disorders. Such disorders include but are not limited to degenerative discs with (i) localized tears or fissures in the annulus fibrosus, (ii) localized disc herniations with contained extrusions, and (iii) chronic, circumferential bulges.

It will be readily apparent to a person skilled in the art that the apparatus and method of use of the apparatus may be used to treat/destroy body tissue in any body cavity or tissue locations that are accessible by percutaneous or endoscopic catheters or open surgical techniques, and is not limited to the disc area. Application of the apparatus and method in all of these organs and tissues are intended to be included within the scope of the present disclosure.

In the drawings and in the following description, the term "proximal", as is traditional, will refer to the end of the apparatus, or component thereof, which is closest to the operator, and the term "distal" will refer to the end of the apparatus, or component thereof, which is more remote or further from the operator.

Figure 2:
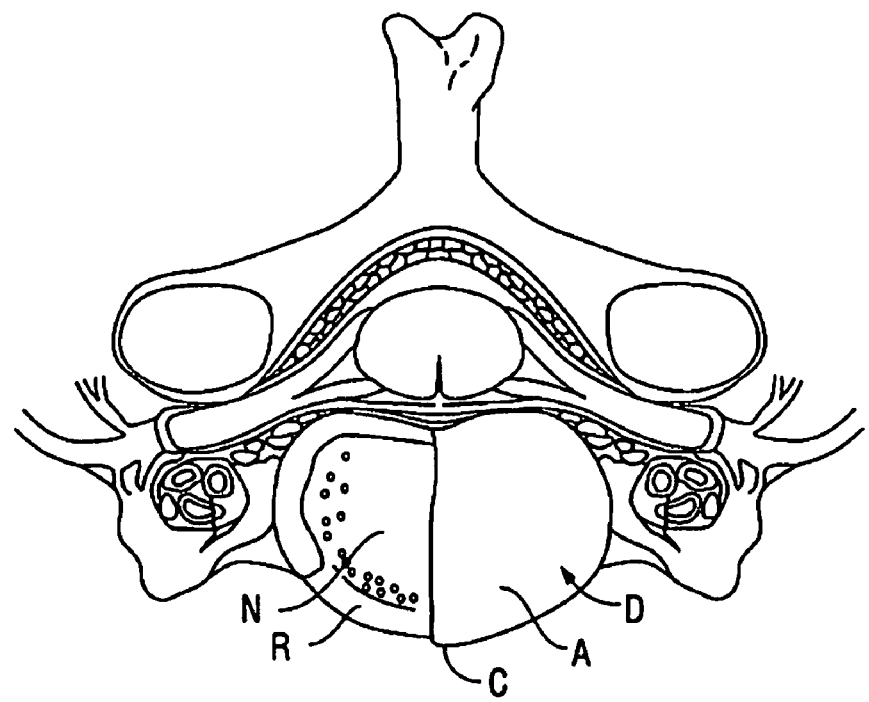
FIG. 2 is a cross-sectional plan view of a cervical disc and vertebra.
Figure 4:
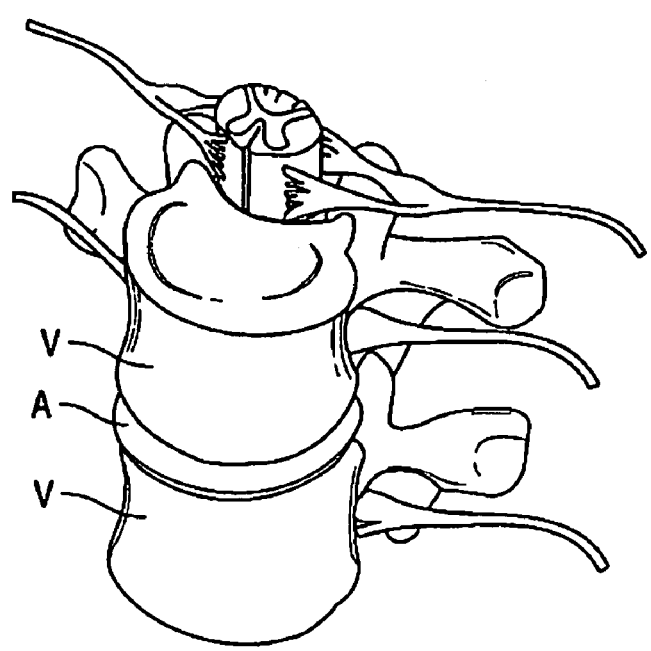
FIG. 4 is an enlarged side view of the area indicated as "4" of the spine of FIG. 3.
Figure 3:
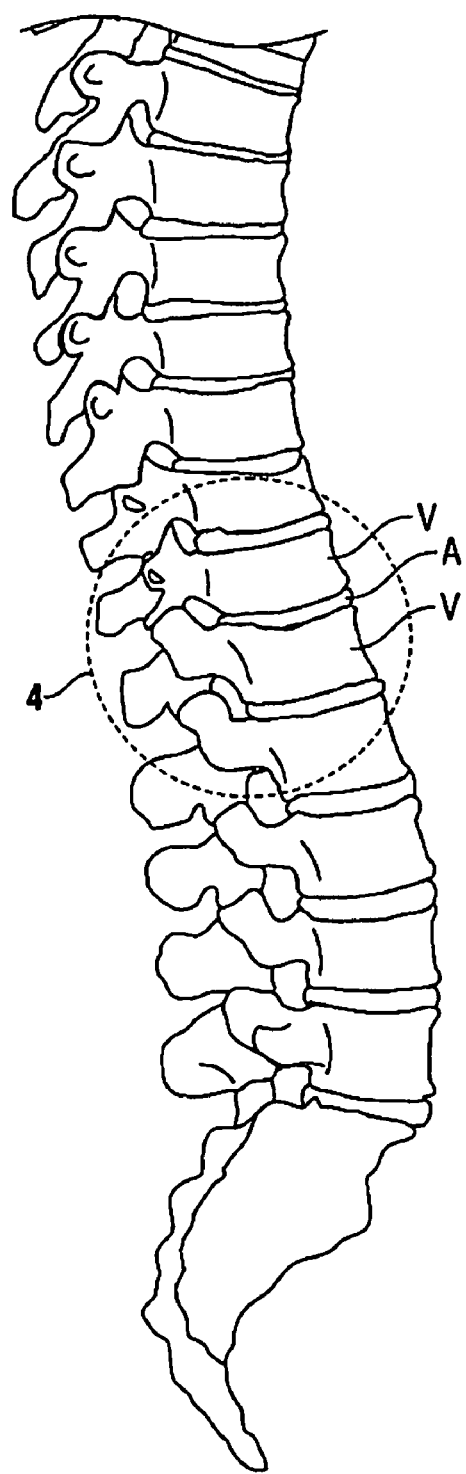
FIG. 3 is a side view of a portion of the spine.

Prior to a detailed discussion of the apparatus and method according to the present disclosure, a brief overview of the anatomy of the intervertebral disc is presented. Accordingly, as seen in FIGS. 1-4, intervertebral disc "D" includes an annulus fibrosus "A" and a nucleus pulposus "N" disposed within annulus fibrosus "A". Annulus fibrosus "A" includes a tough fibrous material which is arranged to define a plurality of annular cartilaginous rings "R" forming the natural striata of annulus fibrosus "A". Nucleus pulposus "N" is made up primarily of an amorphous gel having a softer consistency than annulus fibrosus "A". Nucleus pulposus "N" usually contains 70%-90% water by weight and mechanically functions similar to an incompressible hydrostatic material. The juncture or transition area of annulus fibrosus "A" and nucleus pulposus "N" generally defines, for discussion purposes, an inner wall "W" of annulus fibrosus "A", Disc cortex "C" surrounds annulus fibrosus "A". Posterior, anterior, and lateral aspects of intervertebral disc "D" are identified as "P", "AN" and "L", respectively, with the opposed posterior-lateral aspects identified as "PL". In FIG. 2, a portion of intervertebral disc "D" has been cut away so that half of the vertebral body may be seen.

Figure 6:
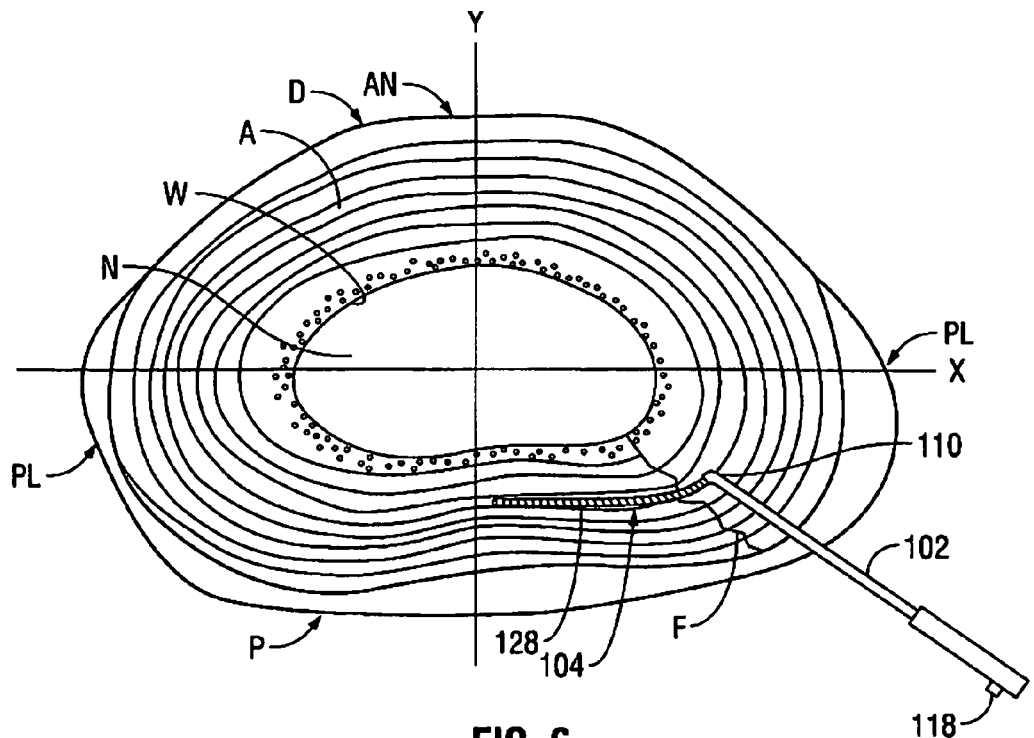
FIG. 6 is a cross-sectional plan view of an intervertebral disc with a portion of an intervertebral apparatus inserted therein according to a method of the present disclosure.

When mechanical stress is put upon a disc or when a disc degenerates with age, fissures, illustrated by cracks "F" in FIG. 6, may occur in the posterior or posterior/lateral portions of disc "D". Problems with nerves, fissures "F" and degenerative discs may give rise to various patient problems, such as back or leg pain originating from the irritation or occurrence of these abnormalities. Moreover, these conditions may ultimately result in conditions such as bulging or herniated discs. By heating and/or using electromagnetic field (EMF) therapy on intervertebral disc "D", preferably, annulus fibrosus "A" in posterior "P" or posterior-lateral "PL" portions, will result in denervation of nerves and/or alterations and thermal ablation of disc structures, which will in turn produce alleviation of pain and healing of the disc. Thus, it is desirable to have a practical and efficient method of placing a thermal or electromagnetic probe in posterior "P" and/or posterior-lateral "PL" portion of disc "D" where these neural and aberrant structures occur for the relief of pain and other disc related problems.

Figure 5:
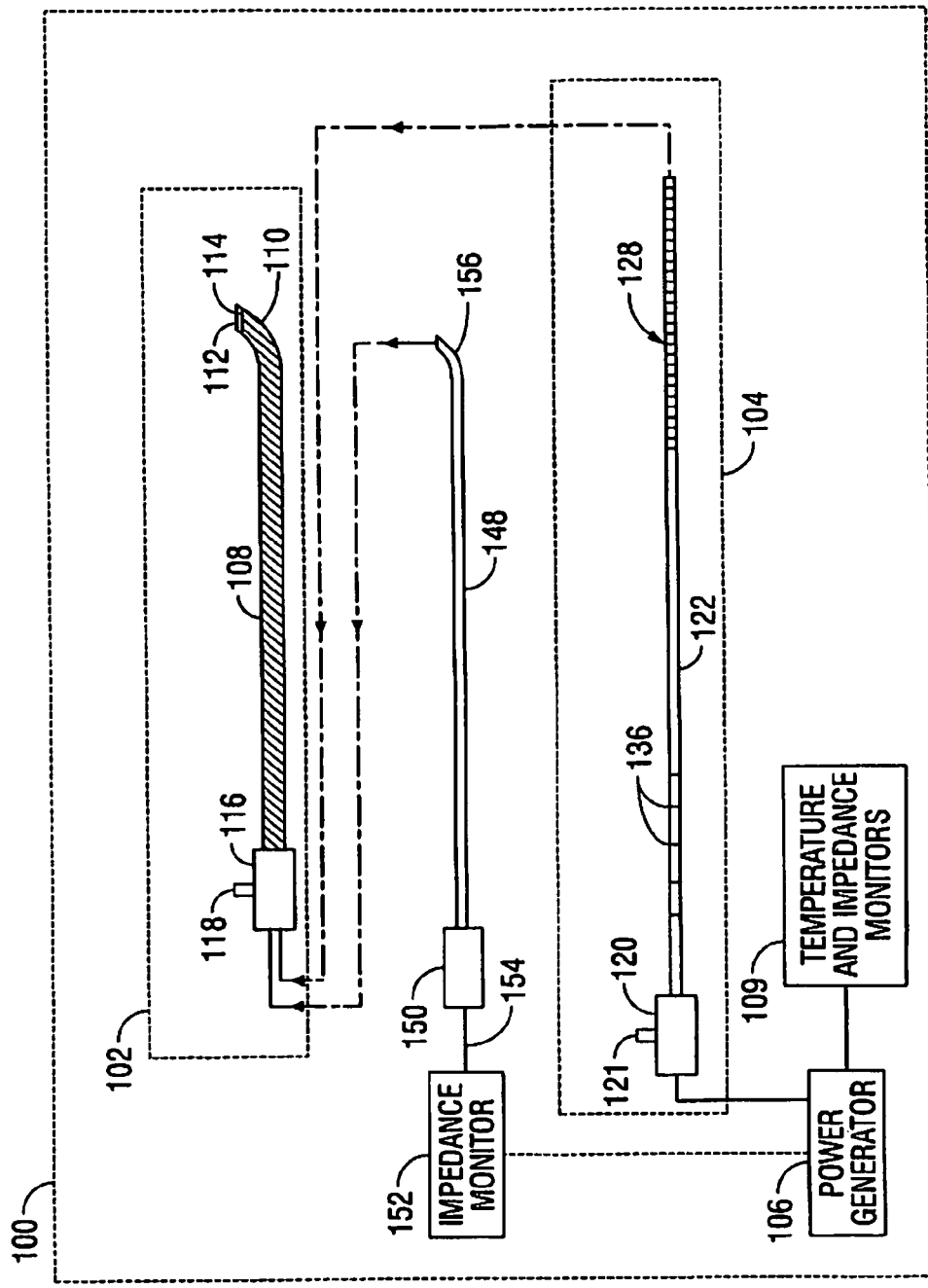
FIG. 5 is a schematic illustration of an intervertebral apparatus, in a disassembled condition, depicting an insertion cannula, a thermal or EMF probe and associated auxiliary electronic components.

With reference to FIG. 5, an apparatus according to the present disclosure is shown and is generally designated as 100. Apparatus 100 includes outer insertion or introducer cannula 102, thermal or EMF probe 104 which is positionable within cannula 102, and a power source 106 which is connected to thermal probe 104. Introducer cannula 102 preferably includes a rigid tubular shaft 108 defining a longitudinal axis "X" and having a rigid curved or arcuate portion 110 adjacent it distal end, angularly offset with respect to the longitudinal "X" axis at an angle ranging from about 15 to about 45°, preferably, about 23°. Shaft 108 is preferably composed of a conductive material such as stainless steel or other suitable composition and is insulated with insulation along most of its length as indicated by the hatching of FIG. 5. Alternatively, shaft 108 may be fabricated from a suitable polymeric material and formed by conventional injection molding techniques. The distal end portion 112 of shaft 108 may be left uninsulated or exposed to permit electrical connection (e.g., for impedance measuring, etc.) to or contact with the tissue as cannula 102 is placed in the tissue. Alternatively, exposed portion 112 may be connected to power source 106 to heat stimulate or micro-thermal generate the tissue to facilitate passage through the tissue.

An extreme distal tip 114 of shaft 108 is preferably sharpened to facilitate penetration into the disc tissue, i.e., through the bone of the cortex "C" and into annulus fibrosus "A". A handle or housing 116 is connected to the proximal end of cannula shaft 108 to facilitate manipulation of cannula 102. Handle 116 may include an index marker 118 to indicate the direction of arcuate portion 110 of cannula 102 such that when thermal or EMF probe 104 is introduced within cannula 102, the surgeon may determine in which azimuthal rotational direction the curve is oriented.

Cannula shaft 108 may have a diameter ranging from a fraction of a millimeter to several millimeters and a length of a few centimeters up to about 20 centimeters or more. Alternatively, cannula shaft 108 may be fabricated from an MRI compatible material, including cobalt alloys, titanium, copper, nitinol, etc. Arcuate portion 110 of cannula 102 may assume a variety of angular orientations depending on the surgical procedure to be performed. In an embodiment for thermal or EMF therapy of the intervertebral disc, arcuate portion 110 is arranged such that thermal or EMF probe 104 is generally delivered from cannula 102 in a substantially orthogonal relation to the longitudinal "X" axis.

Power source or generator 106 may be, for example, a radiofrequency generator providing energy at frequencies between several kilohertz to several hundred megahertz. Power source 106 may have a power output ranging from several watts to several hundred watts, depending on clinical need. Power source 106 may have control devices to increase or modulate power output as well as readout and display devices to monitor energy parameters such as voltage, current, power, frequency, temperature impedance 109, etc., as appreciated by one skilled in the art. Other types of power sources are also contemplated, e.g., including resistive heating units, laser sources, or microwave generators.

Apparatus 100 may preferably include an imaging system (not shown) for potentially monitoring, controlling or verifying the positioning of cannula 102 and/or thermal probe 104. Imaging systems contemplated include X-ray machines, fluoroscopic machines or an ultrasonic, CT, MRI, PET, or other imaging devices. Several of these devices have conjugate elements (not shown), on the opposite side of the patient's body, to provide imaging data. For example, if the imaging system is an X-ray machine, the conjugate element may be a detection device, such as an X-ray film, digital X-ray detector, fluoroscopic device, etc. Use of imaging machines to monitor percutaneously placed electrodes into tissue is commonly practiced in the surgical field.

With continued reference to FIG. 5, apparatus 100 may further include a stylet 148 which is to be used in conjunction with cannula 102. Stylet 148 is positionable within the lumen of cannula 102 and preferably occludes the front opening of cannula 102 to prevent entry of tissue, fluids, etc., during introduction of cannula 102 within intervertebral disc "D". Stylet 148 may include a proximally positioned hub 150 which mates with handle 116 of cannula 102 to lock the components together during insertion. Such locking mechanisms are appreciated by one skilled in the art.

An impedance monitor 152 may be connected, as shown by connection 154, to stylet 148 and therefore communicates electrically with the exposed portion 112 of cannula 102 into which stylet 148 is introduced to monitor impedance of the tissue adjacent the distal end of cannula 102. Alternatively, connection of the impedance monitor may be made directly to the shaft of cannula 102 whereby impedance measurements are effectuated through the exposed distal end of cannula 102. Once the combination of stylet 148 and cannula 102 are inserted into the body, impedance monitoring assists in determining the position of cannula tip 112 with respect to the patient's skin, cortex "C" of disc "D", annulus fibrosus "A", and/or nucleus "N" of disc "D". These regions will have different impedance levels which are readily quantifiable.

For example, for a fully insulated electrode or cannula with an exposed area of a few square millimeters at the cannula end, the impedance will change significantly from the position of the tip near to or contacting cortex "C" of disc "D" to the region where the tip is within annulus fibrosus "A" and further where the tip is within nucleus "N" of disc "D". Differences of impedance may range from a few hundred ohms outside disc "D", to 200 to 300 ohms in annulus fibrosus "A", to approximately 100 to 200 ohms in nucleus "N". This variation may be detected by the surgeon by visualizing impedance on meters or by hearing an audio tone whose frequency is proportional to impedance. Such a tone may be generated by monitor 109. In this way, an impedance means is provided for detecting placement of the curved cannula within disc "D". Thus, for example, in an application where the EMF probe 104 is to be inserted between adjacent layers of annular tissue, undesired penetration of the EMF probe 104 and tip portion 112 of cannula 102, through the inner wall "W" of annulus fibrosus "A" and into nucleus pulposus "N", can be detected via the impedance monitoring means.

Stylet 148 can be made from a rigid metal tubing with either a permanent bend 156 at its distal end to correspond to the curvature of arcuate portion 112 of cannula 102 or may be a straight guide wire to adapt to the curvature of cannula 102 when it is inserted within cannula 102. Hubs 116, 120, 150, and connector 154 can take various forms including luer hubs, plug-in-jack-type connections, integral cables, etc.

With reference now to FIGS. 5 and 6, use of apparatus 100, in accordance with a preferred procedure, for thermal treatment of an intervertebral disc, will now be discussed. With reference to FIG. 6, the targeted intervertebral disc "D" is identified during a pre-operative phase of the surgery. Intervertebral disc "D" defines a "Y" plane extending between a posterior rand an anterior side of disc "D", and an "X" plane, perpendicular to the "Y" plane, extending between lateral sides of the intervertebral disc "D," such that the intervertebral disc "D" defines four substantially equal quadrants (see FIGS. 6-9, for example), wherein the posterior "P", anterior "A", and lateral "L" aspects (e.g. posterior-lateral "PL") are disposed within one or more of the quadrants. Access to the intervertebral disc area is then ascertained, preferably, through percutaneous techniques or, less desirably, open surgical techniques.

Cannula 102, with stylet 148 positioned and secured therein, is introduced within intervertebral disc "D", preferably from a posterior or posterior-lateral location, most preferably, a location which is in relative close proximity to, preferably adjacent to, the region of intervertebral disc "D" to be thermally or electromagnetically treated (e.g., fissure(s) "F"), as seen in FIG. 6. It is envisioned that cannula 102 may be utilized without stylet 148.

Impedance monitoring is desirably utilized to determine the position of cannula tip 114 with respect to the patient's skin, cortex "C" of disc "D", annulus fibrosus "A" and/or nucleus "NN" of disc "D". As discussed above, these regions have different and quantifiable impedance levels thereby providing an indication to the user of the position of cannula tip 114 in the tissue. Monitoring of the location of cannula 102 may also be confirmed with an imaging system (not shown). In a preferred procedure, cannula tip 114 of cannula 102 is positioned within annulus fibrosus "A" of intervertebral disc "D" at a posterior lateral "PL" location of disc "D" without penetrating through inner wall "W" and into nucleus "N". As appreciated, a sharpened cannula tip 114 facilitates entry into annulus fibrosus "A".

Thereafter, cannula 102 is angulated to position arcuate end portion 110 of cannula 102 at the desired orientation within annulus fibrosus "A". Confirmation of the angular orientation of arcuate end portion 110 of cannula 102 is made through location of index marker 118 of cannula 102. In one preferred orientation, arcuate end portion 110 is arranged to deliver thermal probe 104 within the posterior section of the intervertebral disc "D".

Figure 7:
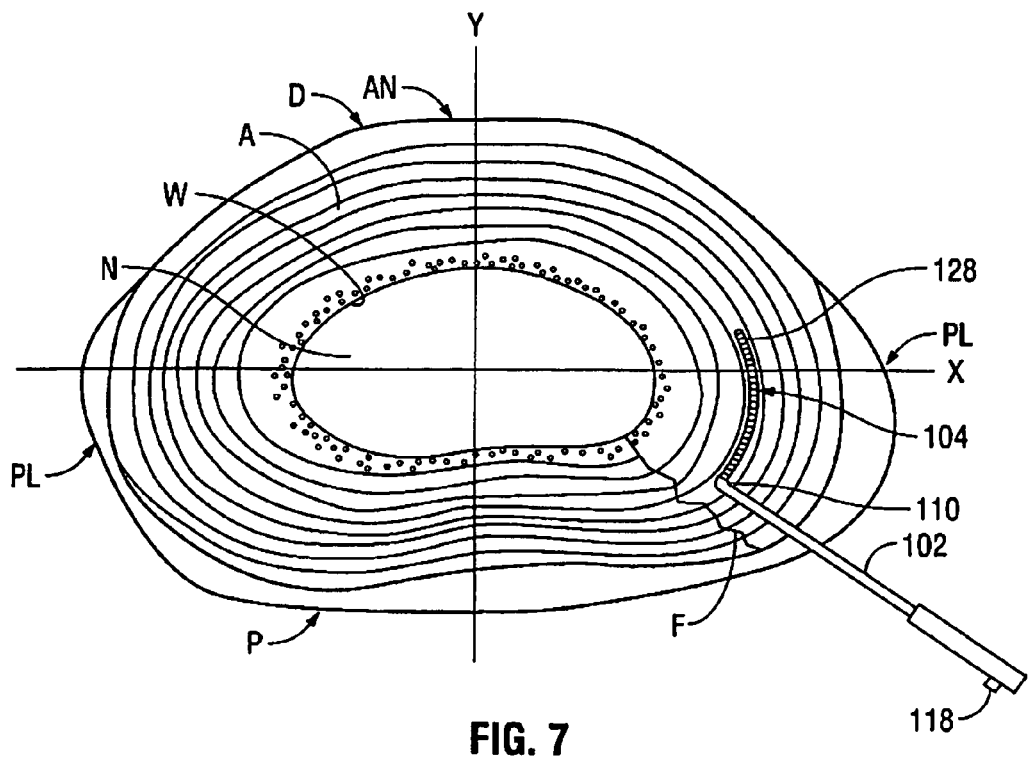
FIG. 7 is a cross-sectional plan view of an intervertebral disc with a portion of an intervertebral apparatus inserted therein according to another method or another step of the present disclosure.

According to another method, as seen in FIG. 7, cannula 102 may be angulated to position arcuate end portion 110 of cannula 102 in another desired orientation within annulus fibrosus "A". In this other desired orientation, arcuate end portion 110 is arranged to deliver thermal probe 104 within the posterior-lateral "L" section of intervertebral disc "D", When so positioned, as will be described in greater detail below, advancement of thermal probe 104 through cannula 102 results in placement of guidable region 128 in the posterior-lateral "PL" section of intervertebral disc "D".

Figure 8:
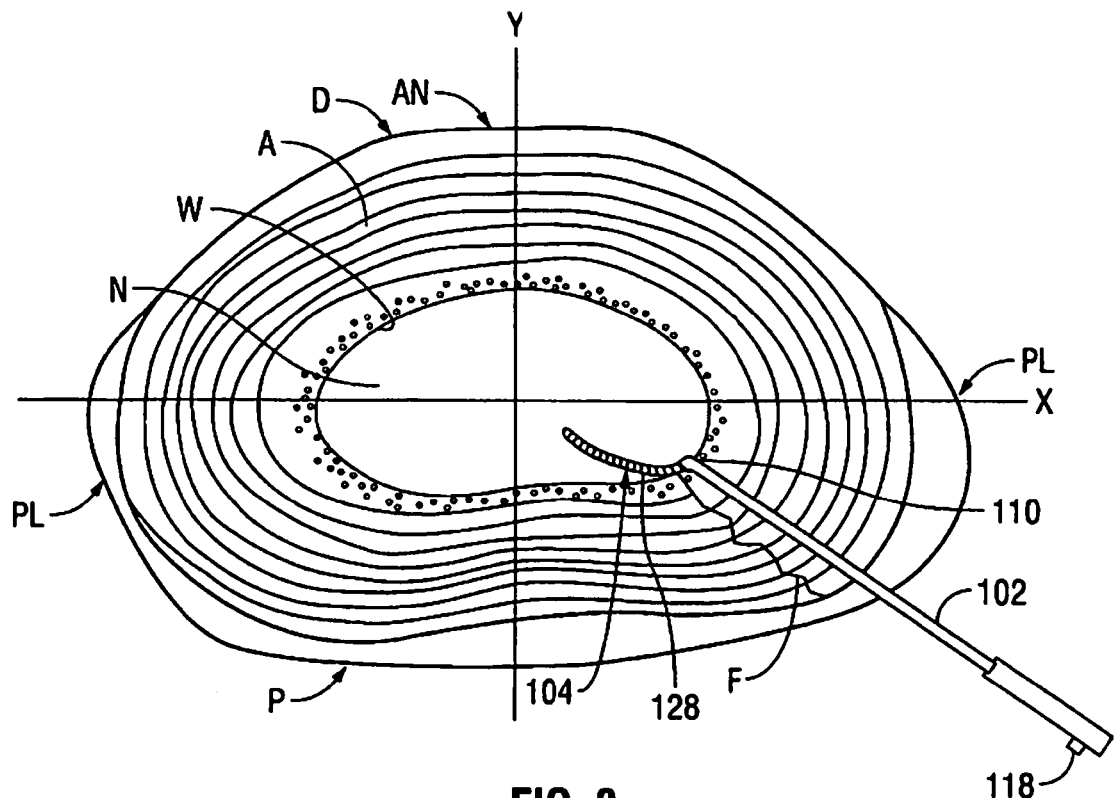
FIG. 8 is a cross-sectional plan view of an intervertebral disc with a portion of an intervertebral apparatus inserted therein according to yet another method or another step of the present disclosure.

According to yet another method, as seen in FIG. 8, cannula 102 may be positioned so as to place arcuate end portion 110 of cannula 102 in yet another desired location and orientation within annulus fibrosus "A". In the other desired orientation and location, arcuate end portion 110 is positioned in close proximity to inner wall "W" of annulus fibrosus "A". When so positioned, as will be described in greater detail below, advancement of thermal probe 104 through cannula 102 results in placement of guidable region 128 in the nucleus "N" of the intervertebral disc "D".

Stylet 148 is then removed from cannula 102. Thermal or EMF probe 104 is positioned within the internal lumen of cannula 102 and advanced through cannula 102. Preferably, the pre-bent orientation of guidable region 128 is arranged to coincide with the arcuate end portion 110 of cannula 102. Confirmation of this orientation may be made with the location of the indexing element 121 of handle 120 (see FIG. 5). Preferably, arcuate end portion 110 is angulated to directly access the posterior-lateral "PL" section of annulus fibrosus "A" without entering nucleus "N". Thermal or EMF probe 104 is thereafter advanced to position guidable region 128 thereof medially through the posterior "P" section of annulus fibrosus "A", desirably adjacent and/or across fissure(s) "F", as seen in FIG. 6. Guidable region 128 of probe 104 is extended by approximately 1.5 cm or less from the distal end of cannula 102.

Alternatively or additionally, as seen in the method of FIG. 7, advancement of thermal or EMP probe 104 results in placement of guidable region 128 thereof laterally along the posterior-lateral "PL" section of annulus fibrosus "A" (e.g., in a direction away from fissure "F". It is further envisioned, as seen in the method of FIG. 8, that thermal or EMF probe 104 may alternatively or additionally be advanced so as to place guidable region 128 thereof into nucleus "N" of intervertebral disc "D".

Figure 9:
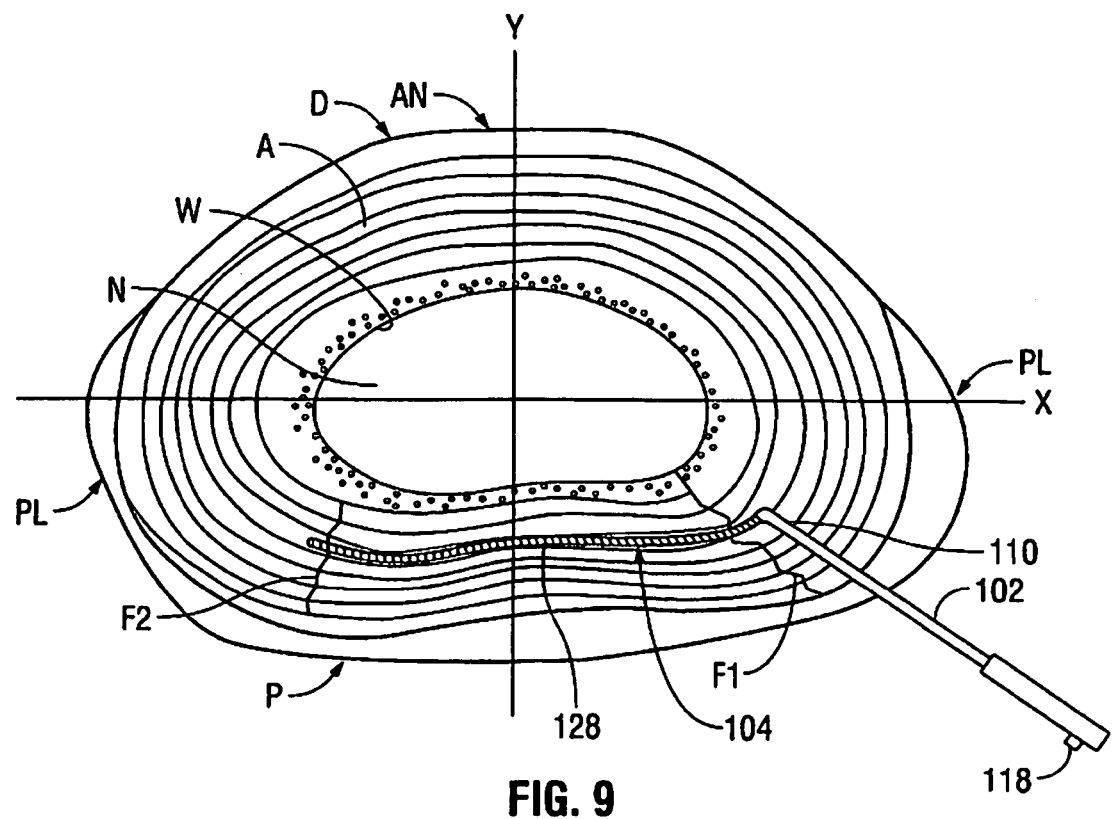
FIG. 9 is a cross-sectional plan view of an intervertebral disc with a portion of an intervertebral apparatus inserted therein according to still another method or another step of the present disclosure.

As seen in FIG. 9, should disc "D" have bilateral fissures "F1, F2" then guidable region 128 of probe 104 may be extended through the posterior "P" section into the contralateral side of the disc "D" in order to place probe 104 adjacent to the secondary fissure "F2". Confirmation of the orientation of arcuate end portion 110 is provided through an index pin or marker adjacent to cannula 102 and can be also monitored through the imaging system.

Following the confirmation that guidable region 128 of probe 104 is properly placed, "Simulation Mode" is selected on power source 106. First, the "Sensory Range" is activated and the amplitude of the simulation is increased until indications of effect and/or stimulation, of the region to be treated, are obtained. The amplitude at which the indications of effect and/or stimulations are obtained, of the region to be treated, is then noted. In the event that the "Sensory Range" does not provide a sufficient effect, the "Motor Range" is activated and the amplitude is increased. The noted amplitude dictates the temperature which is selected on the "Automatic Temperature Control" for the treatment of disc "D". Accordingly, the heating cycle for each position of guidable region 128 of probe 104 is dictated by the threshold of the stimulations. For example, if stimulation of the region to be treated occurs below about 0.75V, then a temperature of approximately 60° C. is applied. If, for example, stimulation of the region to be treated occurs between about 0.75V and 1.25V, then a temperature of approximately 65° C. is applied. If, for example, stimulation of the region to be treated occurs above about 1.25V, then a temperature of approximately 70° C. is applied.

Once guidable region 128 of probe 104 is positioned within annulus fibrosus "A" as desired, power source 106 is activated whereby thermal or EMF probe 104 delivers thermal energy and/or creates an electromagnetic field through guidable region 128 adjacent intervertebral disc "D" to produce the thermal and/or EMF therapy in accordance with the present disclosure. Appropriate amounts of power, current or thermal heat may be monitored from the external power source 106 and delivered for a certain amount of time as determined appropriate for clinical needs.

For example, if denervation of nerves surrounding disc "D" is the objective, the tissue adjacent the probe end is heated to a temperature of from about 45° C. to about 60° C. If heating of fissures "F" in disc "D" is the surgical objective, the temperature in the tissue is raised to about 60-75° C. As appreciated, the degree of extension of guidable region 128 from cannula 102 controls the volume of disc tissue heated by probe 104. A thermal sensor (not shown), provided on thermal or EMF probe 104 can provide information concerning the temperature of tissue adjacent the distal end. In an embodiment, the impedance means associated with cannula 102 can provide impedance measurements of the tissue thereby providing an indication of the degree of dessication, power rise, or charring, that may be taking place near tip 134 of thermal probe 104. This indicates the effectiveness of the treatment and guards against unsafe contraindications of the therapy.

Following thermal treatment at this location, cannula 102 is repositioned so that guidable region 128 of thermal probe 104 is guided laterally in annulus fibrosus "A" toward the posterior-lateral "PL" section. Again, following the confirmation that guidable region 128 of probe 104 is properly placed, "Simulation Mode" is selected on power source 106 and the heating cycle is dictated by the threshold of the stimulations. On completion of thermal treatment in this position, cannula 102 is once again adjusted or repositioned so that guidable region 128 of thermal probe 104 may be placed within nucleus "N" of disc "D". A temperature approximately equal to the boiling point of the nucleus "N" and up to approximately 90° C. is applied if stimulation occurs above about 1.5V when the guidable region 128 of thermal probe 104 is placed within nucleus "N".

The apparatus and method of the present disclosure provides significant advantages over the prior art.

Cannula 102 and thermal or EMF probe 104 permits the probe to be inserted through the body, preferably, on the same side as the tear or fissure "F" formed in annulus fibrosus "A" of disc "D". The present method reduces the distance guidable probe 128 must be steered through annulus fibrosus "A".

Additionally, the site of injury and/or the region to be treated receives a higher level of directed RF energy. As a result, the likelihood of effective treatment of the site of injury and/or the region to be treated is increased. This increased effective treatment may include, and is not limited to, for example, multiple RF treatments that ablate the nerve fibers that have grown into the site of injury, as well as the nerve fibers in the outer annulus fibrosus "A" that may be the source of discogenic pain. The increased effective treatment may also include directed RF energy denaturing of the biochemical constituents of the nucleus pulposus to thereby reduce their contribution as a source of pain. Additionally, the directed RF energy may also create a local area of reduced pressure and higher viscosity in the nucleus "N", in the immediate vicinity of the fissure(s) to thereby reduce the likelihood of further extravasations of nuclear material.

In addition, spinal cord and spinal nerve roots are critical tissues that must be spared during thermal treatments. Accordingly, the present method and/or procedure enables a surgeon to identify if these critical structures are in jeopardy of being injured by the procedure.

A further advantage of the present apparatus and method is that by using a curved introduction cannula, a more efficacious direction of the probe may be achieved in the difficult lumbar or lumbar-sacral intervertebral discs. In these approaches, nearby heavy bone structure, such as the iliac crest, can often obscure a placement of a curved probe parallel to the end plates or bony margins of adjacent intervertebral discs. By appropriate angulation and rotation of a curved cannula, the extension of a thermal probe, parallel to the so-called end plates of the intervertebral discs, is made possible with minimal repositioning and manipulation of the introduction cannula.

A further advantage of the present apparatus and method is that it enables simple, minimally-invasive, percutaneous, outpatient treatment of intradiscal pain without the need for open surgery as for example discectomies or spinal stabilization using plates, screws, and other instrumentation hardware. A further advantage of the present disclosure is that it is simple to use and relatively economical. Compared to open surgery, the treatment of the disc by percutaneous electrode placement represents only a procedure of a few hours with minimal hospitalization, and with minimal morbitity to the patient. On the other hand, open surgical procedures often require full anesthetic, extensive operating room time, and longer hospital and home convalescence.

While the above description contains many specific examples, these specifies should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method for relieving pain associated with an intervertebral disc having a disc nucleus pulposus and an outer annulus fibrosus surrounding the nucleus pulposus, the method comprising:

providing an elongated thermal or electromagnetic probe member having proximal and distal ends and defining a longitudinal axis, and having a flexible guidable region adjacent the distal end;

penetrating the elongated thermal or electromagnetic probe member into a portion the intervertebral disc at a location that is immediately adjacent to a region of the intervertebral disc to be thermally or electromagnetically treated, wherein the region of the intervertebral disc to be treated is a tear extending through the annulus fibrosus;

introducing the flexible guidable region of the probe into at least one of the nucleus pulposus and the annulus fibrosus of the intervertebral disc, at a location which is immediately adjacent to the tear;

positioning the flexible guidable region of the probe toward the tear to extend substantially across the tear;

supplying thermal or electromagnetic energy, from an energy source, to heat or induce an electromagnetic field adjacent to the annulus fibrosus sufficient to produce a thermal or electromagnetic effect on the intervertebral disc;

positioning the flexible guidable region of the probe away from the tear to extend substantially opposite the tear;

supplying thermal or electromagnetic energy, from the energy source, to heat or induce an electromagnetic field adjacent to the annulus fibrosus sufficient to produce a thermal or electromagnetic effect on the intervertebral disc;

positioning the flexible guidable region of the probe substantially parallel the tear and toward the nucleus pulpous; and supplying thermal or electromagnetic energy, from the energy source, to heat or induce an electromagnetic field adjacent to the annulus fibrosus sufficient to produce a thermal or electromagnetic effect on the intervertebral disc.

2. A method according to claim 1, wherein the tear defines an axis, and further comprising the step of inserting the probe into the annulus fibrosus in a direction substantially parallel to the axis of the tear.

3. A method according to claim 1, wherein the disc further defines a second plane, the second plane being orthogonal to a first plane, whereby the disc is divided by four quadrants.

4. A method according to claim 3, further including the steps of:

penetrating the elongated thermal or electromagnetic probe member into a quadrant of the disc containing the region to be treated; and introducing the flexible guidable region of the probe into the annulus fibrosus of the intervertebral disc at a location immediately adjacent to the region of intervertebral disc to be thermally or electromagnetically treated, wherein the flexible guidable region initially provides the thermal or electromagnetic treatment to the quadrant of the disc containing the region to be treated.

5. A method according to claim 4, further including the steps of:

supplying thermal or electromagnetic energy, from the energy source, to heat or induce an electromagnetic field adjacent to the annulus fibrosus sufficient to produce a thermal or electromagnetic effect on the intervertebral disc within a quadrant of the disc other than the quadrant of the disc containing the region to be treated.

6. A method for relieving pain associated with an intervertebral disc, the method comprising:

providing an elongated thermal or electromagnetic probe having a flexible guidable region;

penetrating the elongated thermal or electromagnetic probe member into a portion the intervertebral disc that is to be thermally or electromagnetically treated, adjacent to a treatment site;

introducing the flexible guidable region of the probe into the portion the intervertebral disc that is to be thermally or electromagnetically treated, adjacent the treatment site;

positioning the flexible guidable region of the probe in a first location, adjacent to the treatment site of the intervertebral disc;

supplying thermal or electromagnetic energy, from an energy source, to heat or induce an electromagnetic field to produce a thermal or electromagnetic effect on the treatment site of the intervertebral disc;

positioning the flexible guidable region of the probe in a second location, extending across the treatment site of the intervertebral disc; and supplying thermal or electromagnetic energy, from the energy source, to heat or induce an electromagnetic field to produce a thermal or electromagnetic effect across the treatment site.

7. A method according to claim 6, further including the steps of:

positioning the flexible guidable region of the probe in a third location of the intervertebral disc to be thermally or electromagnetically treated; and supplying thermal or electromagnetic energy, from the energy source, to heat or induce an electromagnetic field to produce a thermal or electromagnetic effect at the third location of the intervertebral disc.

8. A method according to claim 7, wherein the third location is disposed within a nucleus of the intervertebral disc.

9. A method according to claim 6, wherein the first and second locations are disposed within an annulus fibrosis of the intervertebral disc.

10. A method according to claim 6, wherein the treatment site is a tear extending through the annulus fibrosis, and the method includes the steps of positioning the flexible guidable region in a first orientation to extend substantially away from the tear during treatment, positioning the flexible guidable region in a second orientation to extend substantially across the tear during treatment, and positioning the flexible guidable region to extend substantially parallel to the tear during treatment.

\* \* \* \* \*